United States Patent [19]

Edwards

[11] Patent Number: 4,472,410
[45] Date of Patent: Sep. 18, 1984

[54] PREVENTING RENAL FAILURE EMPLOYING NICOTINIC ACID

[76] Inventor: K. David G. Edwards, 458 West Broadway, New York, N.Y. 10012

[21] Appl. No.: 213,194

[22] Filed: Dec. 4, 1980

Related U.S. Application Data

[62] Division of Ser. No. 965,059, Nov. 20, 1978, Pat. No. 4,250,191.

[51] Int. Cl.³ .......................................... A61K 31/455
[52] U.S. Cl. .................................................. 424/266
[58] Field of Search ......................................... 424/266

[56] References Cited

PUBLICATIONS

Edwards et al.; Med. J. Aust. (1972) 2, p. 167.
Edwards et al.; Lancet, (1973) 1, p. 1192.
Ibels et al.; British Med. Journal, pp. 552–554 (1976).
Issekutz; Canadian Journal of Physiology+Pharmocology, vol. 49 (1971), pp. 102–105.
Edwards et al.; Aust. NZJ. Med. 4:420 (1976).
Edwards, Artery; 3(2) 135–149 (1977).
Issekutz; C.A. vol. 74 (1971) 110013s.

*Primary Examiner*—Allen J. Robinson
*Attorney, Agent, or Firm*—Natter & Natter

[57] ABSTRACT

A method and substances are featured for reducing the risk of incurring renal damage or failure. Substances useful in the treatment of hyperlipidemia and closely-related vascular conditions have been found to reduce or prevent renal failure. The substances most generally utilized are derivatives of phenoxyacetic acid. These substances are administered from 0.01 to 0.25% by weight of the dietary materials ingested by the host which is equivalent to 0.2 to 6.0 grams per day in man.

2 Claims, No Drawings

PREVENTING RENAL FAILURE EMPLOYING NICOTINIC ACID

RELATED APPLICATION

This application is a division of application Ser. No. 965,059 filed Nov. 20, 1978 and issued Feb. 10, 1981 as U.S. Pat. No. 4,250,191.

This invention relates to a method and substances for protecting against renal failure or damage.

In the past, elevated serum cholesterol and triglyceride concentrations were considered as high risk factors together with cigarette smoking and hypertension for coronary artery disease. This was especially so, when both lipid parameters were elevated simultaneously. Therefore, it was not surprising to find exaggerated incidence of atherosclerosis and coronary heart disease in the human nephrotic syndrome, the advanced stages of which were traditionally accompanied by high lipid levels.

As a countermeasure to coronary and vascular problems, it was suggested that antihyperlipidemic drugs be used. Indeed, recent studies indicate that the drug clofibrate (Atromid - S) gives significant protection against ischaemic heart disease and death in patients with angina pectoris.

Certain studies with patients who had undergone renal transplantation have also revealed that renal failure was usually accompanied by a hypertriglyceridaemia. This hypertriglyceridaemic condition was generally thought to be a secondary condition or complication of the worsening renal state, as reported in the following articles:

Edwards, K. D. G. and Charlesworth, J. A., "Antihyperlipidaemic effects of renal transplantation and antilymphoeyte globulin in uraemic hyperlipidaemia", Med. J. Australia, ii: 167 (1972);

Edwards, K. D. G. and Charlesworth, J. A., "Is control of hyperlipidaemia important in kidney transplantation?", Lancet, i: 1192–1193 (1973); and Ibels, L. S. et al, "Arterial disease in renal allograft recipients", Australia, N.Z.J. Med. 3:436–437 (1973).

After many years of research in this area, it occurred to the inventor that the high level of lipids in the blood might not be a secondary attribute or complication of renal disease, but rather a causative factor contributing to the worsening of the renal condition itself. Accordingly, it was proposed that before the progression of chronic renal failure in humans, a protective antihyperlipidaemic substance could be administered to prevent the renal failure.

Therefore, an experiment was proposed to feed a number of laboratory rats a diet which would encourage a hyperlipidemic condition. In some of these rats, chronic renal failure was induced by injection of puromycin aminonucleoside. The hyperlipidemic rats experienced marked renal failure. Comparative tests with laboratory chow-fed rat controls (hypolipidemic diet) did not show this marked renal failure.

In addition, some of the hyperlipidemic rats were fed an antihyperlipidemic substance (halofenate). These rats exhibited a reduced tendency to renal failure when injected with puromycin aminonucleoside. The study was conducted over a one-year period which would be the equivalent of a thirty-five year span in man.

It was concluded therefore that substances that control or otherwise are helpful in reducing the lipid levels in the blood could also reduce the risk factors in renal failure. These substances could be administered as a protective or prophylactic treatment at the onset of the hyperlipidaemic condition so as to prevent renal failure.

It is an object of this invention to provide a method of reducing the risk of incurring renal failure by prophylactic treatment with at least one antihyperlipidemic substance.

It is another object of this invention to provide a new use for an antihyperlipidemic substance as a prophylactic treatment against renal failure.

It is a further object of this invention to administer a substance used in the treatment of hyperlipidaemias and other closely-related vascular conditions, as a prophylaxis against renal failure.

These and other objects of the invention will be better understood and will become more apparent with consideration to the following detailed description.

In accordance with the invention, it is proposed to administer at least one antihyperlipidemic substance to hosts as a protective or prophylactic treatment against renal failure. This substance is given in quantities approximately 0.03% to 0.07% by weight of the dietary material ingested by the patient.

In the case of a phenoxyacetic acid derivative, such as halofenate, this equates to about one or two grams per day in human hosts. As in the case of L-tryptophan, for example, this equates to approximately 3 to 5 grams per day. The phenoxyacetic acid derivatives are well known antihyperlipidaemic drugs and are also referred to as chlorophenoxyisobutryic acid (clofibrate) - analogs. Chlorophenoxyisobutryic (CPIB) is shown by the following formula:

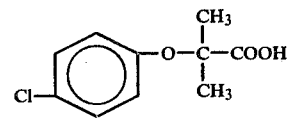

A preferred substance called halofenate is shown below, and is sometimes referred to as an α-p-chlorophenyl-α-m-trifluoro-methylphenoxyacetate or MK-185 fatty acid moiety, (CFPA) the free acid having the formula:

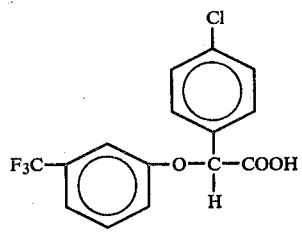

Some substances of this general class are listed below:
clofibrate (Atromid-S)
halofenate
lifibrate
benzafibrate
simfibrate
lenofibrate (lipanthyl)
gemfibrozil
etofibrate Certain amino acids such as L-tryptophan and D-thyroxine are also helpful as antihyperlipidemic substances. L-tryptophan is given by the following formula:

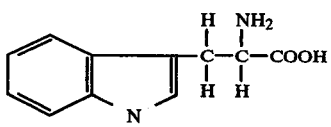

Other useful antihyperlipidemic substances may include activated charcoal, cholestyramine, cholestipol, nicotinic acid, β-sitosterol and terbufibrol, fonlipol (tiadenol), gemcadiol and WY-14,643 oxandrolone. The above is not meant to be a total listing of all the available or useful drugs for the treatment of hyperlipidaemia. Others are known, such as heparin and certain steroids, but these may cause other side effects that reduce their efficacy.

The use of halofenate, a phenoxyacetic acid derivative, as a prophylaxis against renal failure was demonstrated to be statistically significant* ($P<0.05$) in the following tabulated test conducted over the course of one year with laboratory rats (equivalent to 35 years in man):

TABLE
EXAMPLE I

|  | Av. | PTG | PTC | UTPr | 2KW | GFR | RPF |
|---|---|---|---|---|---|---|---|
| LC-CON | (n = 9) | 146 | 90 | 7 | 100 | 100 | 100 |
| CON + 1An | (7) | 217 | 187* | 17* | 124* | 86 | 85 |
| CON + 2An | (2) | 211 | 119 | 7 | 123 | 91 | 101 |
| SLR | (15) | 489* | 128* | 5 | 107 | 103 | 95 |
| SLR + 1An | (10) | 479* | 127* | 20* | 149* | 61* | 66* |
| SLR + 2An | (5) | 287* | 241* | 41* | 135 | 14* | 16* |
| SLR + Hal | (12) | 162 | 88 | 5 | 98 | 83 | 84 |
| SLR + Hal + 1An | (12) | 154 | 94 | 5 | 116 | 92 | 96 |
| SLR + Hal + 2An | (4) | 119 | 180 | 25 | 176 | 39 | 41 |

*protection ($P < 0.05$)

wherein:
PTG and PTC are plasma triglycerides and total cholesterol mg/dl;
$UTP_r$ is urinary total protein/creatinine, mg/mg;
2KW is 2-kidney wt. (2KW, % n);
GFR is the Glomerular Filtration Rate, (14C-inulin clearance): and
RPF is Renal Plasma Flow (3H-PAH clearance, ml/min, % n);
1An is 1 i.p.i. of puromycin aminonucleoside (90 mg/kg.);
2An is 2 i.p.i. of puromycin aminonucleoside (90 mg/kg., 3 mo. intervals);
SLR is sucrose (60% or 45%)/lard (5% or 20%)-fed rats;
LC-CON is lab chow-fed controls (normal, n.);
Av. is the number of rats measured to provide the average values at the right; and
Hal is halofenate 0.05% of sucrose lard diets.

From the above study, it was determined that sucrose/lard diets increased PTG and PTC levels and aggravated the degree of chronic renal damage induced by An. Halofenate, a clofibrate analog, largely controlled hyperlipidemia, and protected against chronic proteinuria, nephromegaly and chronic renal failure. Protection was only partial, however, with severe 2 An. disease induced by a double administration of puromycin aminonucleoside.

In another test with laboratory rats over a two-week period, the following data was obtained (acute study):

TABLE
EXAMPLE II

|  | Av. | PTG | PTC | PTrp | UTPr/Cr | BUN |
|---|---|---|---|---|---|---|
| HSL | (n = 8) | 160 | 78 | 22 | 4 | 16 |
| HSL+An | " | 681 | 231 | 10 | 57 | 33 |
| HSL+Trp | " | 102 | 57 | 25 | 6 | 21 |
| HSL+An+Trp | " | 552 | 151* | 15* | 35* | 24* | significant change or *protection ($P < 0.05$)

wherein:
HSL is high sucrose (60%)/lard (5%) diets;
PTrp is plasma tryptophan (mg/ml);
Trp is tryptophan, 1% supplement in HSL diet;
UTPr/Cr is urinary total protein/creatinine; (mg/mg);
BUN is blood urea nitrogen (mg/dl):
An is 1 i.p.i. of aminonucleoside (90mg/kg);
Av. is the number of rats measured to provide the average values at right;
PTG and PTC are plasma triglycerides and total cholesterol (mg/dl).

A significant statistical change ( ) was noted in the various levels of PTG, PTC, PTrp, etc. ($P<0.05$) with the rats receiving a high sucrose/lard (HSL) diet and aminonucleoside injections vis-a-vis rats fed a standard pellet diet (normal, n.). Also, there was a significant statistical change (*) in the (HSL+AN) rats who received tryptophan. It was evident, therefore, that sucrose/lard diets aggravated the degree of acute renal damage induced by the aminonucleoside (a 10-fold v. a 6-fold increase in UTPr/Cr and a 2-fold v. a 1.5-fold elevation of BUN). It was also deduced that tryptophan had renoprotective activity in rats with hyperlipidemia and renal disease.

Because tryptophan in treated rats reduced the levels of lipids to a statistically significant degree in a similar manner as did halofenate in treated rats (Example I), it is logical to conclude that tryptophan and most other antihyperlipidemic agents are useful as prophylactic substances against renal damage and/or failure.

Having thus described the invention, what is desired to be protected by Letters Patent is presented in the following appended claims.

What is claimed is:

1. A method of treating renal failure or damage in a host in need of said treatment comprising administering for one year or more to said host an effective amount for treating renal failure or damage of nicotinic acid.

2. The method of claim 1 wherein the nicotinic acid is administered to the host in substantially daily quantities totalling approximately from 0.2 to 6.0 grams.

* * * * *